United States Patent [19]

Zee-Cheng et al.

[11] 4,310,666

[45] Jan. 12, 1982

[54] ANTI-NEOPLASTIC 1,4-BIS-(SUBSTITUTED AMINOALKYL AMINO)-ANTHRAQUINONES

[75] Inventors: Robert K. Zee-Cheng, Overland Park; Chia-Chung Cheng, Leawood, both of Kans.

[73] Assignee: United States of America, Washington, D.C.

[21] Appl. No.: 50,100

[22] Filed: Jun. 19, 1979

Related U.S. Application Data

[62] Division of Ser. No. 895,082, Apr. 10, 1978.

[51] Int. Cl.³ .................. C07D 241/04; C07C 97/12; C07C 97/24; C07C 97/26
[52] U.S. Cl. .................................. 544/380; 260/378; 260/379; 260/380
[58] Field of Search ................ 260/378, 379, 380; 544/380

[56] References Cited

U.S. PATENT DOCUMENTS

| | | | |
|---|---|---|---|
| 1,014,204 | 1/1912 | Berchelmann | 260/379 |
| 1,911,316 | 5/1933 | Hauser et al. | 260/379 |
| 3,881,865 | 5/1975 | Greenhalgh et al. | 260/378 |
| 3,960,751 | 6/1976 | Moriyama et al. | 260/378 |
| 4,051,155 | 9/1977 | Hoare | 260/379 |
| 4,138,415 | 2/1979 | Murdock et al. | 252/438 |
| 4,197,249 | 4/1980 | Murdock et al. | 260/380 |

FOREIGN PATENT DOCUMENTS 869688 12/1979 Fed. Rep. of Germany .

OTHER PUBLICATIONS

*Chemical Abstracts*, vol. 80, #16443j, 1972, "1,4 Diamino Anthraquinone Dyes" Schmidt.
*Journal of Medicinal Chemistry*, vol. 83, pp. 291–294, "Antineoplastic Agents", Zee-Cheng et al., 1978.
*Chemical Abstracts*, vol. 83, #201736g, 1975 "Interaction of Aminoalkylamino Anthraquinones with Deoxyribonucleic Acid".

*Primary Examiner*—Winston A. Douglas
*Assistant Examiner*—Raymond K. Covington
*Attorney, Agent, or Firm*—Holman & Stern

[57] ABSTRACT

An antineoplastic 1,4-bis-substituted-9-10-anthracenedione having the formula

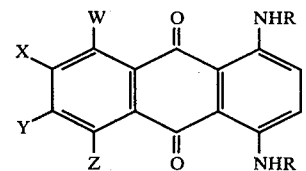

wherein W, X, Y and Z are each independently selected from the group consisting of hydrogen, OH, $NH_2$, $OCH_3$, $N(CH_3)_2$, F, Cl, Br, I, alkyl groups containing from 1–8 carbon atoms, glucosides, phenyl and substituted phenyl, and R is selected from the group consisting of alkyl amino groups containing from 1–8 carbon atoms, alkylaminoalkyl groups containing from 1–8 carbon atoms, substituted alkylamino-alkyl groups containing from 1–8 carbon atoms, and substituted aminoaryl groups.

5 Claims, No Drawings

ANTI-NEOPLASTIC 1,4-BIS-(SUBSTITUTED AMINOALKYL AMINO)-ANTHRAQUINONES

This is a divisional application of U.S. patent application Ser. No. 895,082, filed Apr. 10, 1978.

BACKGROUND OF THE INVENTION

This invention relates to 1,4-bis-(substituted aminoalkylamino)-anthraquinones, and more particularly to the same as anti-neoplastic agents against animal neoplasms. 1,4-bis-substituted anthraquinones have long been known in the prior art as dyes. For example, U.S. Pat. No. 2,050,661 teaches a process for preparing 1,4-diaminoanthraquinone which is suitable for use for dying cellulose esters and ethers or for coloring fats, oils, waxes, and the like. U.S. Pat. No. 1,199,176 teaches the use of 1,4-bis-(alpha, beta-diphenolethylamino) anthraquinone and the like for dying wool and other animal fibers.

A method for the production of 1,4-bis-(substitued aminoalkylamino)-anthraquinones is also known in the art ("The reaction of leucoquinizarines with alkylenediamines", Greenhalgh and Hughs, J. Chem. Society (C), page 1284 (1968)).

Certain naturally occurring substituted anthraquinones, namely, 2,6-bis-substituted and 2,7-bis-substituted anthraquinones, have been found to give indications of possible anti-neoplastic inhibitory effects. Generally, these have been reported as inhibitions of DNA polymerases by intercalation between base pairs of DNA double helix. The intercalation theory has been used as a working hypothesis to explain the activity of many anti-cancer drugs including actinomycin D, daunorubicin, adriamycin, anthramycin, and coralyne. However, certain of these drugs, even though recognized as very promising and definitely showing good inhibitory activity against leukemia as well as solid tumors, have the disadvantage that they or their metabolites cause severe and irreversible cardio toxicity which could be fatal if the accumulated dose of these drugs exceeds a limited amount. Additionally, they are all naturally produced.

Certain in vivo testing systems and protocols have been developed by the National Cancer Institute for testing compounds to determine their suitability as anti-neoplastic agents. These have been reported in *Cancer Chemotherapy Reports*, Part III, Vol. 3, No. 2, (1972), Deran, Greenberg, MacDonald, Schumacher and Abbott. These protocols have established standardized screening test which are generally followed in the field of testing for antineoplastic agents. Three of these systems are particularly significant to the present invention. These are lymphoid leukemia L1210, lymphocytic leukemia P388 and melanotic melanoma B16. All of these neoplasms are found in mice. Initial screening is usually done with P388 leukemia and B16 melanoma if the initial tests appear promising. Generally, good antineoplastic activity shown in these protocols by a percentage increase of mean survival times of the test animals over the control animals is predictive of similar results in human leukemias. A mean survival time ratio of test over control (with the control group representing 100%) of 125% is considered necessary to demonstrate antineoplastic activity by the substance being tested. Further detailed description of these protocols is presented hereinbelow in the detailed description of the invention.

OBJECTS OF THE INVENTION

It is a primary object of the invention to provide new compounds for treating animal neoplasms in an animal neoplasm-bearing host including humans.

It is a further object of the present invention to provide as the primary object, a synthetically-made substance.

It is a still further object of the present invention to provide for the primary object a substance having lower toxicity and fewer side effects.

It is yet a further object of the present invention to provide novel 1,4-bis-(substituted aminoalkylamino)-anthraquinones.

Still another object of the present invention is to provide effective compounds for treating the highly predictive P388 leukemia in mice, the highly predictive B16 melanoma in mice.

The above and other objects are achieved in accordance with the present invention by anti-neoplastic 1,4-bis-substituted anthracenediones having the formula

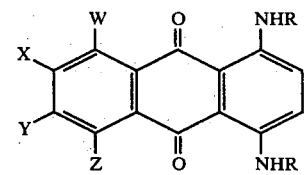

wherein W, X, Y and Z are each independently selected from the group consisting of hydrogen, OH, $NH_2$, $OCH_3$, $N(CH_3)_2$, F, Cl, Br, I, alkyl groups containing from 1-8 carbon atoms, glucosides, phenyl and substituted phenyl, and R is selected from the group consisting of alkylamino groups containing from 1-8 carbon atoms, alkylaminoalkyl groups containing from 1-8 carbon atoms, substituted alkylaminoalkyl groups containing from 1-8 carbon atoms, and substituted aminoaryl groups.

Some of the above groups have been found to be especially effective. These include the compounds in Table 1.

TABLE 1

|   | W | X | Y | Z | R |
|---|---|---|---|---|---|
| a. | OH | H | H | OH | $(CH_2)_2-NH-(CH_2)_2-OH$ |
| b. | H | H | H | H | $(CH_2)_2NH(CH_2)_2OH$ |
| c. | H | H | H | H | $(CH_2)_2NHCH_2CH_3$ |
| d. | H | H | H | H | $(CH_2)_2NHCH_3$ |
| e. | H | H | H | H | $(CH_2)_2NH_2$ |
| f. | H | H | H | H | $(CH_2)_2N\underset{\smile}{\overset{\frown}{\phantom{N}}}NH$ |
| g. | H | H | H | H | $(CH_2)_3NH(CH_2)_2OH$ |

DETAILED DESCRIPTION OF THE INVENTION

Generally, the method of preparation of the 1,4-bis (substituted aminoalkylamino) anthraquinones was based on that described by Greenhalgh and Hughes, J. Chem. Society (C), Page 1284, 1968. This involves condensation of leucoquinizarins (II) with an excess amount of the appropriate amines at 50° to 55° C. followed by air oxidation of the dihydro intermediates (III) to the desired products (IV).

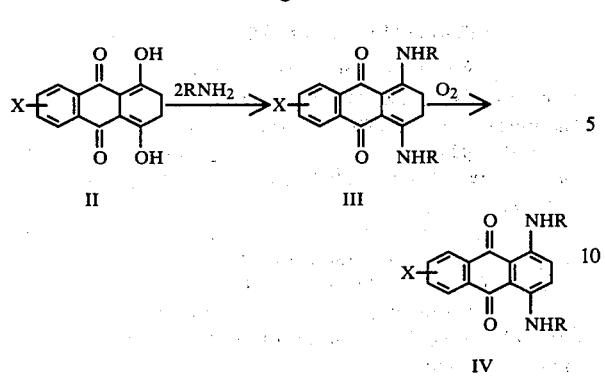

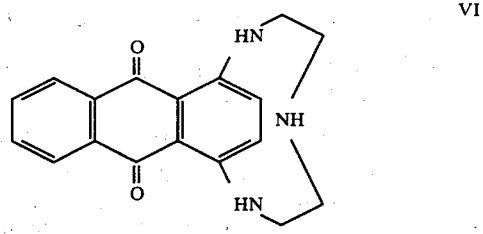

Since the intermediates III and products IV have distinct and different UV absorption in ethanol (III are usually green, with λ max at 465 and 490 nm, whereas the bright blue IV have λ max at 580 and 630 nm) the absorption change of the reaction mixture is used to monitor the course of the reaction and to estimate the purity of the products. The products, which are soluble in water, strongly stain skin, fiber, and even plastic material. The intense dark color of solutions of these compounds often affect purification processes.

Oxidation of the dihydro intermediates III to the aminoanthraquinones IV proceeded readily in most cases and sometimes can even be realized during recrystallization of the crude dihydro intermediates III or upon standing of III in solution. Hence, attempts to isolate the pure dihydro intermediates III, even under nitrogen, proved to be difficult. For example, attempted isolation of the dihydro intermediate of 1,4-bis (hydroxyethyl-aminoethylamino) anthraquinone gave an 80% yield of a crude compound, melting point of about 130°–132° C. It was, understandably, still contaminated with the final product. At a higher reaction temperature of about 100° C., the product readily cyclized to form compound V.

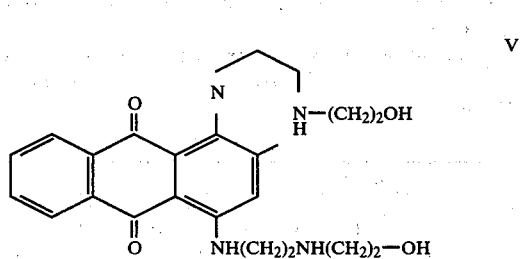

For the preparation of many target compounds, therefore, the reaction temperature must be kept below 55° C., preferably at 50° C.

Some difficulties were encountered during the preparation of the dihydro intermediate 1,4-bis (2-aminoethylamino) anthraquinone because of the presence of a primary amine function on the side chains and the insolubility of the intermediate in the particular reaction solvents used (ethanol and $CH_3CN$). The dihydro intermediate was eventually obtained but subsequent oxidation by air in $CH_3CN$ yielded a high-melting solid, melting point about 308°–310° C., which was only sparingly soluble in common organic solvents such as ethanol or $CHCl_3$. Elemental analysis indicated the presence of only three nitrogen atoms in the molecule and suggested VI as one of the possible structures of the product.

Apparently compound VI was formed by an intramolecular condensation of the two terminal chains with the elimination of $NH_3$. The desired compound e (Table I), melting point of 174°–176° C., was obtained in 23% yield by repeated recrystallizations of the dihydro intermediate from $CH_3CN$ according to the method noted above of Greenhalgh and Hughes.

EXAMPLE 1

Preparation of 1,4-dihydroxy-5,8-bis[[2-(hydroxyethyl)amino]ethyl-]amino-9,10-anthracenedione.

The preparation of 1,4-dihydroxy-5, 8-bis[[2-(hydroxyethyl) amino]ethyl]amino-9,10-anthracenedione (compound a, Table I) was carried out as follows: To 10 g (0.036 mole) of 5,8-dihydroxyleucoquinizarin (commercially available from [Bayer AG, 509 Leverkusen, Beyerwerk, West Germany], purified by continuous extraction with dioxane under nitrogen) was added dropwise, under nitrogen with cooling and stirring, 38 g (0.36 mole) of 2-(2-aminoethylamino)ethanol. When a homogeneous paste was obtained, the reaction mixture was heated at 50°–55° C. in an oil bath for two hours. It was allowed to stir overnight. The mechanical stirring rod was replaced (the stirring rod was rinsed with 4×50 ml of ethanol, the ethanol washings were added to the mixture) by a glass sparge tube and dry air (passed through a tube containing Drierite) was bubbled through the reaction mixture (the entire system was under a slightly reduced pressure) by connecting the top of the condenser to a water aspirator. This mold oxidation reaction was carried out at 55°–60° C. for approximately 2–3 hours. The color of the syrup gradually changed from purple to a bright blue. The mixture was then allowed to stand overnight at room temperature. The resulting dark blue solid was collected by filtration through a sintered glass funnel. The solid product washed with ethanol (2×20 ml), petroleum ether (3×50 ml) and dried to give 4.6 g (20% yield) of Compound a, m/p/ 158°–160° C. An analytical sample was prepared by recrystallization of the crude product from a mixture of ethanol and petroleum ether, m.p. 160°–162° C. $\lambda_{max}^{EtOH}$ 244 (log ε4.64), 279 (4.31), 525 (3.70), 620 (4.37) and 660 nm (4.38).

Anal. Calculated for $C_{22}H_{28}N_4O_6$: C, 59.50; H, 6.34; N, 12.61. Found: C, 59.55; H, 6.56; N, 12.33

EXAMPLE II

Preparation of 1,4-Bis[[2-(ethylamino)ethyl]amino]-9,10-anthracenedione

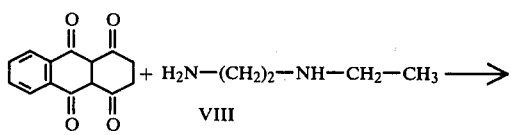

VII

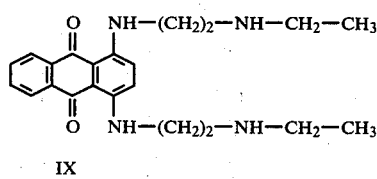

IX

A mixture of 4 g (0.9165 mole) of 1, 4, 9, 10-tetrahydroxyanthracene (leucoquinizarin) VII and 23 g (0.26 mole) of N-(2-aminoethyl)ethylamine VIII was heated to 50° C. under $N_2$ for ninety minutes. The mixture was cooled and allowed to stand overnight. To it was added 100 ml of methanol. A stream of dry air was bubbled through the mixture at 50° C. for two hours. Blue crystals, which separated from the reaction mixture after standing, were collected by filtration and washed with 10 ml of ethyl acetate followed by 10 ml of hexane. The product was purified by recrystallization from a mixture of chloroform, and heptane to give 3.5 g (56% yield) of IX, m.p. 118°–120° C.

Anal: Calculated for $C_{22}H_{28}N_2O_4.2H_2O$: C, 63.44; H, 7.74; N, 13.45. Found C, 63.61; H, 7.79; N, 13.68.

EXAMPLE III

Preparation of 1,4-Bis[[2-methylamino)ethyl]amino]-9,10 anthracenedione

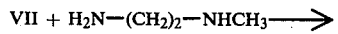

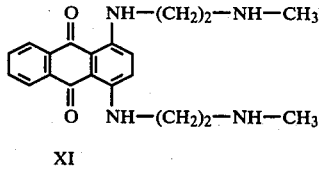

XI

Twenty-two grams (0.29 mole) of N-(2-aminoethyl) methylamine (X) was added dropwise into 10.0 g (0.045 mole) of VII under nitrogen with stirring in 15 min. After the addition was complete, the mixture was stirred for an additional 30 min., then heated at 50°–55° C. for three hours. It was then cooled and 100 ml of ethanol was added. Dry air was bubbled through the mixture at 45°–50° C. for three hours. It was allowed to stand overnight and to it was added 40 ml of ethanol and 20 ml of Skelly solve F (petroleum ether, bp 35°–60° C.). The mixture was stirred for thirty minutes and the solid product was collected by filtration. It was washed successively with ethanol (2×5 ml) and Skelly solve F (2×50 ml) and dried to give 8.2 g (52% yield) of XI, mp 120° C. An analytical sample was prepared by recrystallization of 1.2 g of XI from 50 ml of chloroform and 100 ml of Skelly solve F, mp 119°–121° C. Anal. Calculated for $C_{20}H_{24}N_4O_2. \frac{1}{2}H_2O$: C, 66.46; H, 7.06; N, 15.50. Found: C, 66.29; H, 7.11; N, 15.31

EXAMPLE IV

Preparation of 1,4-bis[2-aminoethyl)amino]-9,10-anthracenedione

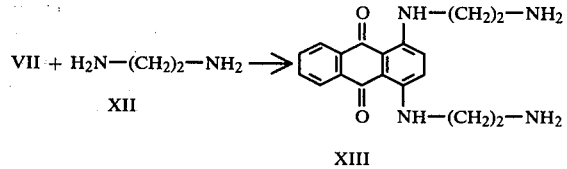

XIII

A mixture of 14.5 g (0.06 mole) of VII and 150 ml of ethylenediamine (XII) was heated under $N_2$ for one hour at 50° C. Dry air was bubbled through the mixture at 50° C. for forty-five minutes. The mixture, after standing overnight, deposited XIII which was collected by filtration, washed successively with acetonitrile (3×30 ml) and diethyl ether (2×50 ml) and dried to give 17 g of crude XIII, mp 165°–168° C.

Its ultraviolet absorption spectrum showed the presence of dihydro derivatives. Three recrystallizations from acetonitrile gave 5.9 g (23% yield) of purified XIII, mp 174°–176° C.

Anal. Calculated for $C_{18}H_{20}N_4O_2$: C, 66.65; H, 6.21; N, 17.27. Found: C, 66.45; H 6.36; N, 17.10.

The antineoplastic activity of the various compounds was determined in in vivo testing following the protocols developed by the National Cancer Institute reported by Deran et al in *Cancer Chemotherapy Reports*, part 3, Vol. 3, No. 2, (1972). These specific test systems were lymphoid leukemia L1210, lymphocytic leukemia P388 and melanotic melanoma B16. The key test result noted is the mean survival time ratio of test animals over control animals which is hereinafter noted as percentage increase of life span of test over control (percent ILS). As noted above, a percent ILS of 125% is considered to show good antineoplastic activity.

Activity against lymphocytic leukemia P388 is tested by implanting ascitic fluid in $BDF_1$ mice. Treatment with the compound begins twenty-four hours after the implant. As noted above, the results are expressed as a percent increase in life span or survival time. The innoculum site for screening is ip and the compound is administered ip daily for nine days. The implant size is 0.1 ml of diluted ascitic fluid containing $10^6$ cells. The number of survivors of the test group on day 6 is checked. All deaths of test animals after day 6 are not considered to be due solely to drug toxicity. Testing ends on day 30. The mean animal weight difference between the test group and the control group is computed between days 1 and 5. At the completion of testing the percent ILS is computed for all test groups with greater than 65% survivors on day 5. A percent ILS value of less than 85% indicates a toxic test, a percent ILS of greater than 125% is considered to demonstrate antineoplastic activity. Any survivor of the test group on the day of evaluation (day 30) is recorded as a cure.

Activity against lymphoid leukemia L1210 is tested by implanting ascitic fluid into $BDF_1$ mice. Treatment begins twenty-four hours after the implant. The results are expressed as a percentage of increased life span of the test animals over the control animals. The inoculum site is ip and the compound is administered ip. The implant size is 0.1 ml of diluted ascitic fluid containing $10^5$ cells. As with P388, the toxicity check date is day 6 and the experiment is run for thirty days. Mean animal weight is also checked between days 1 and 5 and the percent ILS is computed at the end of the experiment. Any survivors of the test group on day thirty are considered to be cures.

Activity against melanotic melanoma B16 is tested by implanting a tumor homogenate ip in $BDF_1$ mice. The treatment begins twenty-four hours after the ip implant and the results are expressed as a increased percentage of life span of the test animals over the control animals. The drug is administered ip daily for nine days. To prepare the homogenate, 1 gram of tumor is mixed with 10 ml of cold balanced salt solution and homogenized. 0.5 ml of the tumor homogenate is implanted ip. The check date for compound toxicity is day 5 and the experiment runs until day 60.

All dosages are in milligrams per kilogram of body weight of test animal per injection. The mean survival time of the test animals is computed and ratioed with the mean survival time of the control animals and the result is expressed as a percentage (%ILS). Other specific information regarding the animal selection and animal care, randomization of animals in the testing, specific preparation and administration of test materials, selection of doses, propagation of tumor lines, tumor quality control, specific techniques of tumor transplantation, and the exact calculational method for test evaluation can be found in the above noted reference to Deran et al, which is incorporated herein by reference.

ANTINEOPLASTIC TESTING EXAMPLES

In addition to the compounds listed in Table 1, the following compounds with noted structure are presented:

TABLE II

| | W | X | Y | Z | R |
|---|---|---|---|---|---|
| h. | H | H | H | H | $(CH_2)_2NH(CH_2)_2CH_3$ |
| i. | H | H | H | H | $(CH_2)_2N\langle\text{pyrrolidinyl}\rangle$ |
| j. | H | H | H | H | $(CH_2)_2NH(CH_2)_2NH(CH_2)_2OH$ |
| k. | H | H | H | H | $(CH_2)_2S(CH_2)_2OH$ |
| l. | H | H | H | H | $(CH_2)_5OH$ |
| m. | H | H | H | H | $(CH_2)_2$—(3,4-dimethoxyphenyl) |

The following results were obtained testing for activity against lymphocytic leukemia P388:

TABLE III

ACTIVITY AGAINST P388

| Compound | Dose mg/kg | Survival | Wt. Diff. gm | % ILS | Cures |
|---|---|---|---|---|---|
| a | 2 | 6/6 | −0.6 | 280 | 5/6 |
| | 1 | 5/6 | −0.6 | 277 | 3/6 |
| | 0.5 | 6/6 | −2.0 | 299 | 4/6 |
| | 0.25 | 6/6 | −2.3 | 280 | 2/6 |
| | 0.12 | 6/6 | −1.4 | 200 | |
| | 0.06 | 6/6 | −1.7 | 208 | |
| b | 32 | 6/6 | −5.9 | 81 | |
| | 16 | 6/6 | −3.9 | 275 | 3/6 |
| | 8 | 6/6 | −2.0 | 276 | 4/6 |
| | 4 | 6/6 | 0 | 275 | 3/6 |

TABLE III-continued

ACTIVITY AGAINST P388

| Compound | Dose mg/kg | Survival | Wt. Diff. gm | % ILS | Cures |
|---|---|---|---|---|---|
| c | 25 | 11/12 | −4.8 | 132 | 1/12 |
| | 12.5 | 5/6 | −2.8 | 168 | |
| | 6.25 | 6/6 | −2.2 | 149 | |
| | 3.13 | 6/6 | −2.3 | 142 | |
| d | 12.5 | 6/6 | −1.9 | 200 | |
| e | 25 | 6/6 | −2.6 | 215 | |
| | 12.5 | 6/6 | −1.1 | 174 | |
| | 6.25 | 6/6 | −1.1 | 159 | |
| | 3.13 | 6/6 | −019 | 107 | |
| | 1.56 | 6/6 | −1.6 | 137 | |
| | 0.78 | 6/6 | −1.3 | 150 | |
| f | 50 | 10/12 | −217 | 134 | |
| | 25 | 12/12 | −1.0 | 137 | |
| | 12.5 | 12/12 | −1.1 | 117 | |
| | 6.25 | 6/6 | −0.4 | 125 | |
| g | 100 | 11/12 | −2.6 | 98 | 1/12 |
| | 50 | 12/12 | −2.1 | 133 | |
| | 25 | 11/12 | −2.1 | 130 | |
| | 12.5 | 6/6 | −1.4 | 117 | |
| | 6.25 | 6/6 | 0.9 | 101 | |
| h | 100 | 6/6 | −2.6 | 124 | |
| | 50 | 6/6 | −1.7 | 125 | |
| | 25 | 6/6 | −0.8 | 118 | |
| i | 100 | 12/12 | −4.5 | 128 | |
| | 50 | 12/12 | −2.9 | 110 | |
| | 25 | 6/6 | −3.6 | 104 | |
| j | 100 | 15/18 | −2.6 | 120 | |
| | 50 | 18/18 | −1.3 | 112 | |
| | 25 | 18/18 | −1.6 | 110 | |
| k | 100 | 6/6 | −2.2 | 94 | |
| | 50 | 6/6 | −1.4 | 86 | |
| | 25 | 6/6 | −1.6 | 95 | |
| l | 100 | 6/6 | −4.0 | 88 | |
| | 50 | 6/6 | −1.5 | 78 | |
| | 25 | 6/6 | −1.4 | 88 | |
| m | 400 | 6/6 | −2.9 | 91 | |
| | 200 | 6/6 | −3.2 | 101 | |
| | 100 | 6/6 | −1.7 | 86 | |

Certain of these compounds were tested against Melanotic Melanoma B16 and Lymphoid Leukemia L1210, the data being presented in Tables IV and V respectively:

TABLE IV

ACTIVITY AGAINST B16

| Compound | Dose | % ILS | Cures |
|---|---|---|---|
| e | 16 | 281 | 8/10 |
| | 8 | 280 | 6/10 |
| | 4 | 280 | 6/10 |
| a | 1 | 503 | 7/10 |
| | 0.5 | 466 | 4/10 |

TABLE V

ACTIVITY AGIANST L1210

| Compound | Dose | % ILS |
|---|---|---|
| b | 125 | 272 |
| | 12.5 | 227 |
| | 6.25 | 156 |

As can be seen from the data in Table III, all of the 1,4-bis(substituted aminoalkylamino) anthraquinones showed at least some antineoplastic activity against P388. A %ILS of greater than 125 is considered good antineoplastic activity.

Some of the results are especially noteworthy. Namely, with the absence of the second amino group (compounds pounds k, l, and m) no activity was evidenced. Apparently, the nitrogen atom in center of the side chain plays an important role in antileukemic activity. No activity is noted when this nitrogen atom is replaced by a methylene unit (even though compound 1 retains the same chain length) or by a sulphur atom. The insertion of an additional ethyl amino unit into the side chain as in compound j, drastically reduces the activity below the marginal level. The distance between the nitrogen atoms appears to have significance which is apparent in the comparison between the results of compound g and compound b. Further importance of the nitrogen atom in the center of the side chain is demonstrated by changing the original secondary amino function to a tertiary amino function. Compound i is only marginally active when compared with compound b. The activity of compound f is slightly there above probably due to the presence of the binding terminal. On the other hand, compound e, which contains primary amino groups at the end of both side chains, still remains good, although not as high as compound b.

Suprisingly excellant antileukemic activity is obtained in compound a (note the extremely low dosage levels both for activity against P388 and activity against B16). This compound is more soluble in water than compound b and appears to require less than one-tenth of the optimum dose of compound b to produce good activity. Compound e additionally shows excellent activity against B16 with a high rate of cures (survivors at the end of day 30 of the test group.)

It should now be apparent that the objects initially set forth have been successfully achieved. Moreover, while there is shown and described present examples of the invention, it is to be distinctly understood that the invention is not limited thereto but may be otherwise variously embodied and practiced within the scope of the following claims. Accordingly, what we claim is pounds k, l, and m) no activity was evidenced. Apparently, the nitrogen atom in center of the side chain plays an important role in antileukemic activity. No activity is noted when this nitrogen atom is replaced by a methylene unit (even through compound 1 retains the same chain length) or by a sulphur atom. The insertion of an additional ethyl amino unit into the side chain as in compound j, drastically reduces the activity below the marginal level. The distance between the nitrogen atoms appears to have significance which is apparent in the comparison between the results of compound g and compound b. Further importance of the nitrogen atom in the center of the side chain is demonstrated by changing the original secondary amino function to a tertiary amino function. Compound i is only marginally active when compared with compound b. The activity of compound f is slightly there above probably due to the presence of the binding terminal. On the other hand, compound e, which contains primary amino groups at the end of both side chains, still remains good, although not as high as compound b.

Surprisingly excellent antileukemic activity is obtained in compound a (note the extremely low dosage levels both for activity against P388 and activity against B16). This compound is more soluble in water than compound b and appears to require less than one-tenth of the optimum dose of compound b to produce good activity. Compound e additionally shows excellent activity against B16 with a high rate of cures (survivors at the end of day 30 of the test group).

Since these compounds show good results against P388, L1210, and B16 which, as noted, are predictive of good results in humans, the compounds disclosed herein should be operative against human leukemias and the like.

It should now be apparent that the objects initially set forth have been successfully achieved. Moreover, while there is shown and described present examples of the invention, it is to be distinctly understood that the invention is not limited thereto but may be otherwise variously embodied and practices within the scope of the following claims.

What we claim is:

1. A substituted anthracenedione having the formula

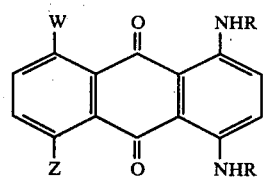

wherein R is —$(CH_2)_2 NHR^1$ and W and Z are each selected from the group consisting of H and OH, and when W and Z are both H, $R^1$ is selected from the group consisting of —$CH_2CH_2CH_3$ and —$CH_2CH_2CH_2CH_3$ and when W and Z are both OH, $R^1$ is —$CH_2OH$.

2. The anthracenedione of claim 1, wherein W and Z are both OH and $R^1$ is $CH_2OH$.

3. The anthracenedione of claim 1, wherein W and Z are both H and $R^1$ is $CH_2CH_2CH_3$.

4. The anthracenedione of claim 1, wherein W and Z are both H and $R^1$ is $CH_2CH_2CH_2CH_3$.

5. An anthracenedione compound of the formula

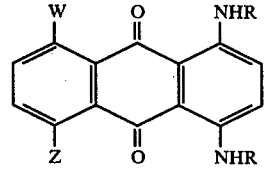

wherein W and Z are each selected from the group consisting of H and OH and R is

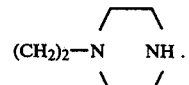

* * * * *